United States Patent [19]

Miwa et al.

[11] Patent Number: 5,183,838
[45] Date of Patent: Feb. 2, 1993

[54] ACID ANHYDRIDE COMPLEX AND PROCESS FOR PRODUCING SAME, AND COMPOSITION CONTAINING SAME

[75] Inventors: Takao Miwa, Katsuta; Takayoshi Ikeda, Tohkai; Shunichi Numata, Hitachi; Koji Fujisaki, Hitachi; Hisae Shimanoki, Hitachi, all of Japan

[73] Assignees: Hitachi, Ltd.; Hitachi Chemical Company, Ltd., both of Tokyo, Japan

[21] Appl. No.: 724,777

[22] Filed: Jul. 2, 1991

Related U.S. Application Data

[63] Continuation of Ser. No. 567,160, Aug. 14, 1990.

[30] Foreign Application Priority Data

Sep. 1, 1989 [JP] Japan .................................. 1-224445

[51] Int. Cl.$^5$ .................... C08K 5/15; C07D 493/02
[52] U.S. Cl. .................................. 524/109; 549/241
[58] Field of Search .......................... 524/109; 549/241

[56] References Cited

U.S. PATENT DOCUMENTS 4,271,079  6/1981  Maeda et al. ..................... 528/93

OTHER PUBLICATIONS

G. M. Bower and L. W. Frost, "Aromatic Polyimides", Journal of Polymer Science: Part A, 1, 3135-3150 (1963).

Primary Examiner—Joseph L. Schofer
Assistant Examiner—Wu C. Cheng
Attorney, Agent, or Firm—Antonelli, Terry, Stout & Kraus

[57] ABSTRACT

An acid dianhydride complex which is characterized in anti-hydrolysis, good stability, and high solubility in an organic solvent, is prepared by a reaction of a basic organic compound having a donor number of at least 20 and being free from an active hydrogen atom in the molecule and a carboxylic dianhydride compound.

7 Claims, 12 Drawing Sheets

ACID ANHYDRIDE COMPLEX AND PROCESS FOR PRODUCING SAME, AND COMPOSITION CONTAINING SAME

This is a continuation of application Ser. No. 567,160, filed Aug. 14, 1990, which is now pending.

BACKGROUND OF THE INVENTION

(1) Field of the Industrial Utilization

The present invention relates to an acid anhydride complex and a process for producing same, and to the composition etc. containing same.

The complex of the present invention can be utilized for the stabilization of acid anhydride compounds during storage, for the improvement of solubility of the acid anhydride compounds to organic solvents, for the viscosity control of polyamic acids, for the technology which is applicable to the manufacturing processes of an electronic device with the composition, varnishes, films, fibers, each of which is containing the acid anhydride complex, and the acid anhydride complex itself.

(2) Description of the Prior Art

An acid anhydride has superior characteristics as a cross-linking agent, a monomer for synthesis of polymers. But, an acid anhydride has strong reactivity in general, and cautious consideration is required for its storage and the condition of its usage. Especially, it is a big problem in the industry that an acid anhydride reacts with moisture in the air and loses its reactivity. For example, an acid anhydride has superior characteristics as a hardner of an epoxy resin, but its utilization is restricted by easiness of causing hydrolysis.

In case of synthesis of polyamic acids etc., hydrolysis of the acid anhydride causes lowering of reactivity as a monomer, and causes a problem to prevent the polymer from getting higher degree of polymerization. Hitherto, according to such unstability, the usage of an acid anhydride have been restricted in spite of its superior characteristics. Therefore, at the time of using an acid anhydride, a special treatment such as storage in dry condition, reactivation by heating just before the using, dehydration of a solvent, are required to prepare for the unstability of the acid anhydride.

In case of synthesis of a polyamic acid etc., the degree of polymerization changes greatly depending on the equivalent ratio of the acid anhydride monomer and a reactant monomer such as an amine. That is, the molecular weight increases to infinity theoretically at the exact equivalent ratio and decreases sharply with deviating the ratio from the equivalence. Accordingly, the molecular weight of the polymer can be controlled easily by controlling the equivalent ratio. A solution of an oligomer having small molecular weight is easy in handling because of its low viscosity even with a high concentration. But, a film having small molecular weight has a problem in mechanical strength.

On the other hand, a solution of a polymer having large molecular weight produces generally a strong film, but the solution has a problem that slight increment of the concentration of the solution causes sharp increment of viscosity and make it impossible to work with the solution.

The solubility of the acid anhydride mentioned above is very poor, for instance, an acid anhydride is soluble very slightly even in N-methylpyrrolidon which is recognized as having the most preferable solubility, and the small solubility is deemed as a big problem in use of acid anhydrides, but there have not been any suitable means to solve the problem.

At the present, a polymer solution having large molecular weight and having easiness in handling even with high concentration and also of superiority in heat resistance, mechanical strength, and resistance to chemicals after it is hardened, is needed widely. A method to use an oligoamic acid obtained by making the molecular weight of polyamic acid small, and a method to use an imide oligomer and an isoimide oligomer both of which have good solubility responds to the need mentioned above. The methods mentioned above made it possible to use a high concentration-low viscosity solution. The usage of the solution is aimed to make it easy to coat in spin coating etc. by using an oligomer solution, and to obtain a superior coating film by causing a reaction at the reactive end groups of the oligomer by heat treatment to get finally a large molecular weight polymer. As for the reactive end groups, a partially esterified acid anhydride, an ethynyl group, a vinyl group, and a biphenylene group etc. have been investigated. For instance, an electronic device manufactured with an oligomer having vinyl group or acetylene group as an end group of the molecule was disclosed in the Japanese Patent Application Laid-Open No. 60-120723 (1985).

A complex crystal having a molar ratio of 1:1 of pyromellitic acid (PMDA) and N,N-dimethylacetamide(DMAC) is described in the Journal of Polymer Science (Part II, vol. 1, pp. 3135–3150). But there are not any description on the properties of the complex and whether it may be convertible to polyimide.

SUMMARY OF THE INVENTION

(1) Objects of the Invention

An acid anhydride has such problems as it is unstable in storage condition, and as difficulty to control the molecular weight of the polyamic acid because of strong reactivity with organic compounds such as amines, and hardly soluble to organic solvents. The acid anhydride complex and polyamic acid complex which are obtained by the present invention resolves such problems of acid anhydride mentioned above, and it is possible to use properly depending on the objects and the condition of the usage.

The one of the objects of the present invention is to provide a new acid anhydride complex and a method of producing same.

The another object of the present invention is to provide a composition, a varnish, a film, a coating etc., each of which contains the acid complex.

The another object is to provide a composition, a varnish, a film, a coating etc., each of which contains the polyamic acid complex, in which a part of the acid anhydride complex reacted with diamine.

The another object of the present invention is to provide a method to produce a polyimide layer, which is necessary for production of an electronic device, with the acid anhydride complex and the polyamic acid complex described above.

(2) Methods Solving the Problems

The objects mentioned above are achieved by acid anhydride derivatives having a carbonyl carbon with a controlled electrophilic reactivity. The feature of the present invention is a complex comprising a base substance B having a donor number of at least 20 and an acid anhydride Ar, and the complex is presented by the general formula, Ar.aB(where $2 \geq a > 1$)

The base substance is free from an active hydrogen atom in the molecule in order to not open the acid anhydride.

A carboxylic acid dianydride used in the present invention is an carboxylic acid dianhydride such as pyromellitic dianhydride (PMDA), benzophenone tetracarboxylic dianhydride (BTDA),3,3',4,4'-biphenyl tetracarboxylic dianhydride (s-BPDA), 3,3',4,4'-biphenylsulfone tetracarboxylic dianhydride (DSDA), 2,2-bis(3,4-dicarboxyphenyl) hexafluoropropane tetracarboxylic dianhydride (6FDA), methylpyromellitic dianhydride, dimethylpyromellitic dianhydride, trifluoromethylpyromellitic dianhydride, bis (trifluoromethyl) pyromellitic dianhydride, 3,3',4,4'-oxydiphenylene tetracarboxylic dianhydride etc. The acid dianhydrides mentioned above are used separately or together depending on the necessity.

In the present invention, an expression "donor number" is defined by a definition described on page 21-29 of the book entitled "Youeki Han-nou no Bunshikan Sougosayou" (Published in 1986 by Gakkai Shuppan Center, Translated by Ohtaki Hitoshi et al.) translated from a book of "Donor-Acceptor Approach to Molecular Interaction" (V. Gutmann, 1978). That is, a donor number is defined as the value of Molar enthalpy of a reaction between $10^{-3}$M SbCl$_5$ in dichloroethane which is selected as a standard acceptor and a donor (D).

Especially, in the case of using a basic organic substance having a donor number of at least 25, the production of a complex is easier in the reaction mentioned above. A basic organic substance, that is an electron donor used in the reaction is such substances having a donor number of at least 20 as tetrahydrofuran(THF), trimethylphosphate(TMP), tributylphosphate(TBP) etc. Especially effective substances having a donor number of at least 25 are such as dimethylformamide(DMF), N-methylpyrrolidon(NMP), N-dimethylacetamide(DMA), dimethylsulfoxide(DMSO), N-diethylformamide(DEF), N-diethylacetamide(DEA), N-methylacetamide, pyridine(PY), hexamethylphosphate triamide(HMPA), tetramethylurea, triethylamine(TEA), etc. In addition, γ-propiolactam and ε-caprolactam etc. are used. The electron donors are used separately or together.

The reactivity of an acid anhydride is generally controlled by a method of hydrolysis to a carboxylic acid or a method of esterification with an alcohol. But, in case of using the methods, the acid anhydride is stabilized too much to require generally heating up to nearly 200° C. for the reactivation. Therefore, the methods have been used in extremely limited area.

An acid anhydride complex obtained by the present invention is able to recover its activity as an acid anhydride easily with heating. Moreover, the complex is extremely stable at moderate temperature which is, it depends on the kinds of complex, generally under 150° C., in some cases under 80° C.

As a result that a complex accepted electrons from an electron donor the degree of δ+ of the carbonyl carbon in the acid anhydride is decreased. The reactivity of the complex for an electrophilic reaction such as hydrolysis and acylation etc. is controlled by the degree of δ+.

The case of using a complex is different from the case wherein the reactivity is lowered by hydrolysis or esterification, and an aimed reaction is easily caused by heating. Therefore, a method of stabilization by the present invention does not harm any of the reactivity of an acid anhydride. Accordingly, a method to produce a complex disclosed in the specification is extremely superior as a stabilizing method of an acid anhydride. Additionally, as a result of investigation on the stability of a complex, it is revealed that such a basic substance having a donor number of at least 25 and N-methylpyrrolidon, dimethylsulfoxide, triethylamine, and pyridine etc. gives specially good stability to the complex.

Tetracarboxylic dianhydride has generally very poor solubility to organic solvents in a condition not forming a complex, and only slightly soluble to an organic solvent such as N-methylpyrrolidon etc. Therefore, a solvent using in a reaction is strictly limited. On the other hand, the solubility of an acid anhydride complex related to the present invention is improved significantly, and the complex is soluble easily to tetrahydrofuran which is practically not used hitherto for acid anhydrides. Thus, an acid anhydride complex obtained by the present invention is very effective to the improvement of solubility. An acid anhydride complex related to the present invention is an electron donor-accepter complex with electron donor as a complex former, which combines to one of the carbon atoms of the carbonyl group of the acid anhydride by a cordinate bond.

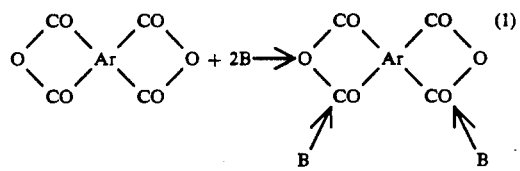

If there are too many molecules of electron donor around one acid anhydride molecule, for example, the case that an acid anhydride is dissolved in a solvent of electron donor, electron donor molecules surround one molecule of the acid anhydride and cause solvation which prevent the formation of a cordinate bond. In the case described above, the formation of the acid anhydride complex is not completed and, even if the solution is heated, the equivalent ratio of an acid anhydride and an electron donor in a complex is nearly 1:1 at most and the yield is less than 30%. To make the equivalent ratio larger than 1:1, it is necessary to make an acid anhydride contact with an electron donor in the gaseous state. For instance, a contact of an acid anhydride with a vapourized electron donor causes a sufficient reaction without making solvation. In other case, the reaction occures by adding dropwise of a small amount of an electron donor to an acid anhydride powder with agitation under heating condition. And, another case is a dropwise addition of an electron donor under a heating condition to a liquid in which an acid anhydride is dispersed in a solvent which dissolve the complex but not the acid anhydride.

In any cases, a complex having an equivalent ratio of 1:2 of an acid anhydride and an electron donor is the most stable against hydrolysis and is superior in solubility to an organic solvent. Depending on the reaction condition, a complex having an equivalent ratio slightly less than 1:2 is obtainable. It is clear that even a complex having a combination ratio slightly less than 1:2 has better stability and solubility than a complex having a combination ratio of 1:1.

It is possible to make a complex with an oligomer by a reaction of a complex obtained by the present invention and an diamine compound.

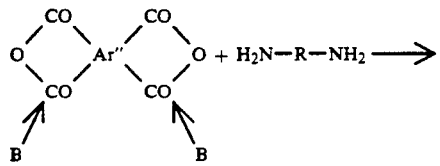

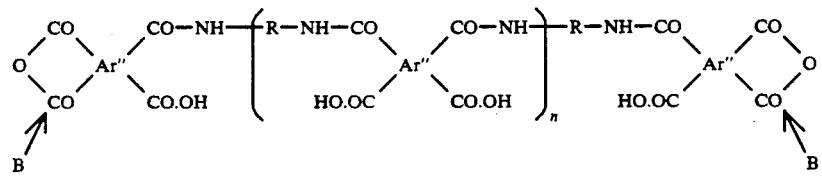

(2)

$(20 \geq n \geq 0,$ specially $10 \geq n \geq 0)$

An acid dianhydride complex obtained by the present invention is related to Ar.2B and a mixture of Ar.2B and Ar.B. By selecting the reaction condition, the mixing ratio of Ar.2B and Ar.B can be changed, and a condition which enable Ar and B react sufficiently increases Ar.2B. It is preferable to make a Ar.aB having at least 1.5 of a for best use of anti-hydrolysis property and solubility of a complex related to the present invention. The Ar.aB having at least 1.5 of a is obtainable by a one step reaction or by a suitable mixing of Ar.2B and Ar.B which are made separately. According to the superior characteristics of the complex, various applications are possible. Polyimide, an important substance in industry, is generally obtained by coating as polyamic acid and subsequent heating and hardening. In the sythesis of a polyamic acid, a precursor of polyimide, a complex related to the present invention is applicable to produce a varnish which has easiness in handling even with high concentration and the same superior mechanical characteristics, heat resistance, and resistance to chemicals after hardening as the case of using high molecular weight polyamic acid. That is, a varnish containing an acid anhydride complex having a monomer or an oligomer structure in the molecule and an equivalent amine compound polymerizes to be a high molecular weight substance by heating which causes a reaction between an acid anhydride complex and an amine compound.

The viscosity of the varnish in the case is far low comparing with that of a conventional polyamic acid varnish of the same concentration, because the viscosity of a high polymer solution is proportional to the three powers of molecular weight. Therefore, a densely concentrated solution can be practically usable by applying a varnish containing the complex mentioned above. Moreover, the varnish after hardening becomes a high molecular weight substance which has the same superior mechanical characteristics, heat resistance, and resistance to chemicals as the case of using a conventional polyamic acid varnish. And of course, it is possible to adjust easily the viscosity of a varnish by changing the content of the complex in the acid anhydride.

It is well known that a polyimide having a rod-like structure has a low thermal expansion coefficient. Therefore, by using a monomer which will produce a polyimide having a rod-like structure, it is possible to obtain a polyimide type resin precursor which has a superior property to produce an insulating film having flat and small thermal stress. It is easily assumed that, if a polyimide obtained finally has a rigid rod-like structure, it has a low thermal expansion coefficient. And, as the low thermal expansion property comes from the structure of skeleton of the main chain, it is obvious that an improvement of the property is possible by introducing a substitute selecting from the group of alkyl, fluorinated alkyl, alkoxyl, fluorinated alkoxyl, aryl, halogen etc., to the monomer.

By copolymerization with other diamine compounds and acid dianhydrides, other improvements are possible such as producing a more flexible polyimide by copolymerization with a polymer having soft structure like as 3,3',4,4'-benzophenone etc. within the range of not losing a property of low thermal expansion, as improving of adhesiveness by copolymerization with a substance such as 1,3 bis [3,4-dicarboxy(1,2,2)bicyclo] tetramethyldicyloxane dianhydride etc. And it is also possible to control ability of wet etching, which is important in a manufacturing process of large scale integrated circuit (LSI), by copolymerization with pyromellitic acid dianhydride and 3,3',4,4'-biphenyltetracarboxylic dianhydride.

An acid anhydride complex related to the present invention is a compound in which an electrophilic reactivity of an acid dianhydride is controlled by formation of a complex with a basic organic compound which is an electron donor having a donor number of at least 20 and being free from an active hydrogen and a carboxylic dianhydride compound, and has a characteristics to recover the reactivity fast by heating. By utilizing the characteristics mentioned above, it is possible to obtain an acid anhydride complex which is stable against hydrolysis reaction and a varnish which produces an polyimide having a property to be a high molecular weight substance by heating and to reveal a superior characteristics although it has low viscosity and densely concentrated low molecular weight substance in a varnish state.

The acid anhydride complex related to the present invention also can be used as a curing agent of an epoxy resin etc. by utilizing a property to be reactive by heating.

A study on the thermal decomposition temperature of the complex obtained by the present invention reveals the results shown in Table 1. The data in Table 1 shows that it is possible to obtain an acid anhydride complex having a property to be active at a desired temperature by suitable selection of an electron donor in the present invention.

On the other hand, the thermal decomposition temperature of s-BPA, which is obtained by hydrolysis of s-BPDA, is 173° C. and its endothermic peak is 257° C.

Besides, the melting point of acid anhydrides are as followings; s-BPDA: 294° C., BTDA: 230° C., PMDA: 228° C., 6FDA: 241° C., DSDA:280° C.,

TABLE 1

| Acid anhydride | Complex former | Endothermic peak (°C.) |
| --- | --- | --- |
| s-BPDA | NMP | 104 |
| " | DMSO | 126 |
| " | PY | 203 |
| " | TEA | 239 |
| BTDA | NMP | 102 |
| " | DMSO | 222 |
| " | PY | 190 |
| " | TEA | 254 |
| PMDA | NMP | 155 |
| " | DMSO | 231 |
| " | TEA | 155 |
| 6FDA | NMP | 208 |
| " | DMSO | 210 |
| " | PY | 221 |
| " | TEA | 257 |
| OPDA | DMSO | 210 |

OPDA: 218° C.

And, the boiling point of electron donors are as followings;

NMP: 203° C., DMSO: 185° C., PY: 115° C., TEA: 89° C.

BRIEF DESCRIPTION OF THE DRAWINGS

FIG. 9 (b) is the liquid chromatogram of the compound produced by a reaction with s-BPDA and ε-caprolactam in 10 hours at 180° C.-200° C., FIG. 9 (c) is the liquid chromatogram of the compound produced by a reaction with s-BPDA and ε-caprolactam in 24 hours at 180° C.-200° C.

DETAILED DESCRIPTION OF THE EMBODIMENTS

EXAMPLE 1

Figure 1:
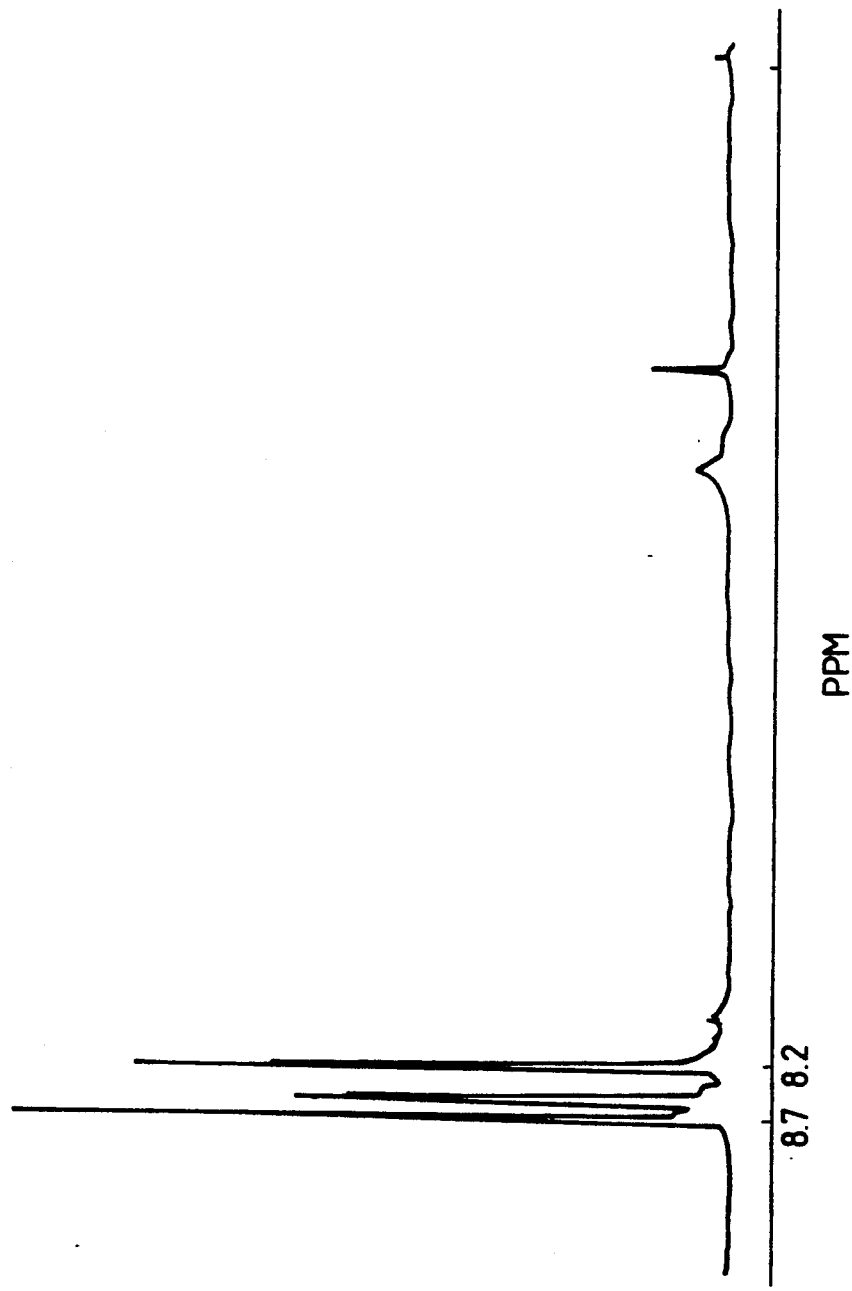
FIG. 1 is the proton Nuclear Magnetic Resonance (NMR) spectrum of s-BPDA.
Figure 2:
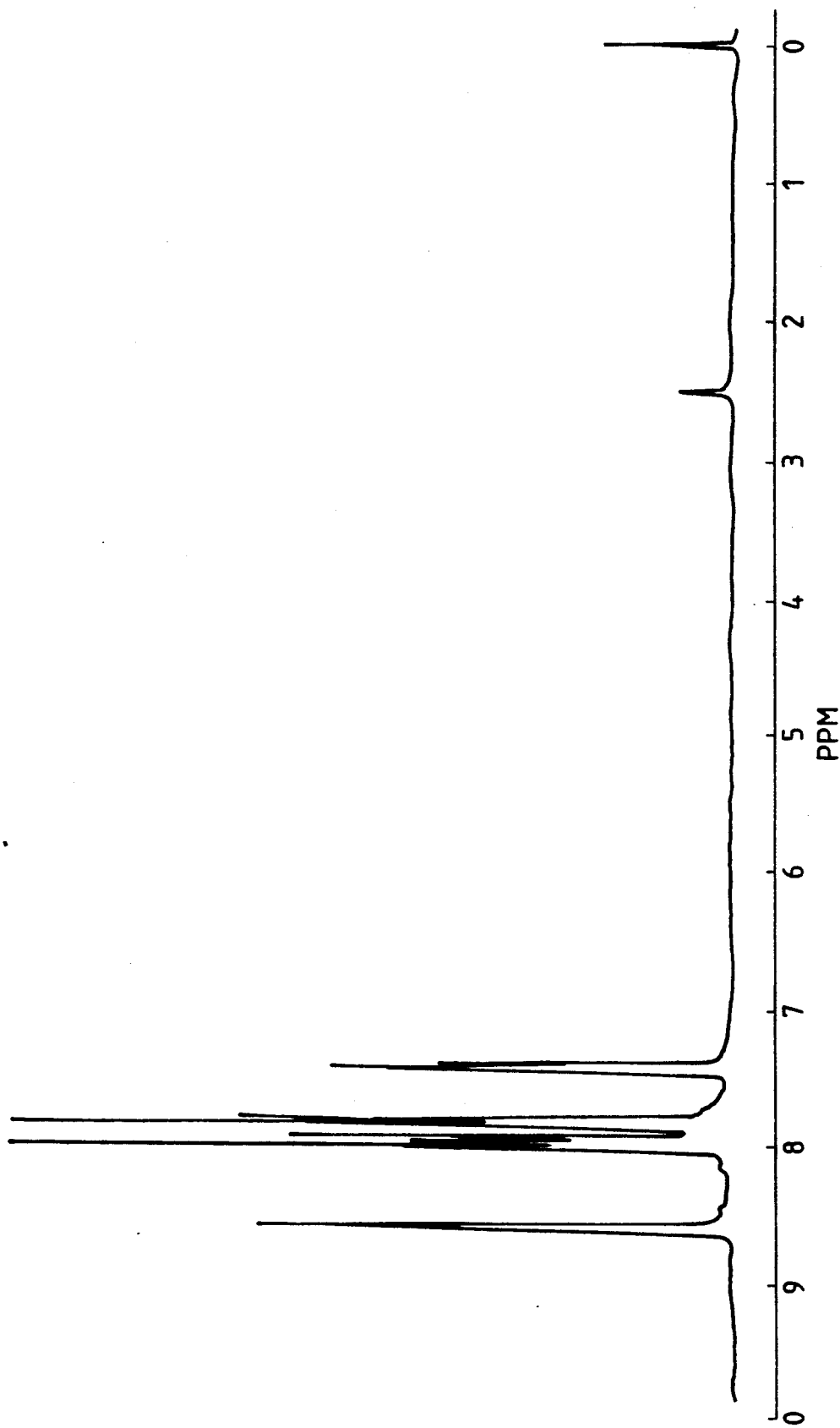
FIG. 2 is the proton NMR spectrum of s-BPDA/PY complex.

An acid anhydride complex having an equivalent ratio 1:2 of s-BPDA:PY was obtained by a reaction with s-BPDA and saturated PY vapour in 40 hours at 100° C. The nuclear magnetic resonance spectrum of s-BPDA is shown in FIG. 1. And the nuclear magnetic resonance spectrum of the obtained complex is shown in FIG. 2. The solvent used at the measurement was DMF-d$_7$. After heating of the acid anhydride complex in DMSO 2 hours at 120° C., the yield of the acid anhydride complex was 50%. And after heating of the acid anhydride complex in PY 1 hour at 100° C., the yield of the acid anhydride complex was 60%.

EXAMPLE 2

Figure 3:
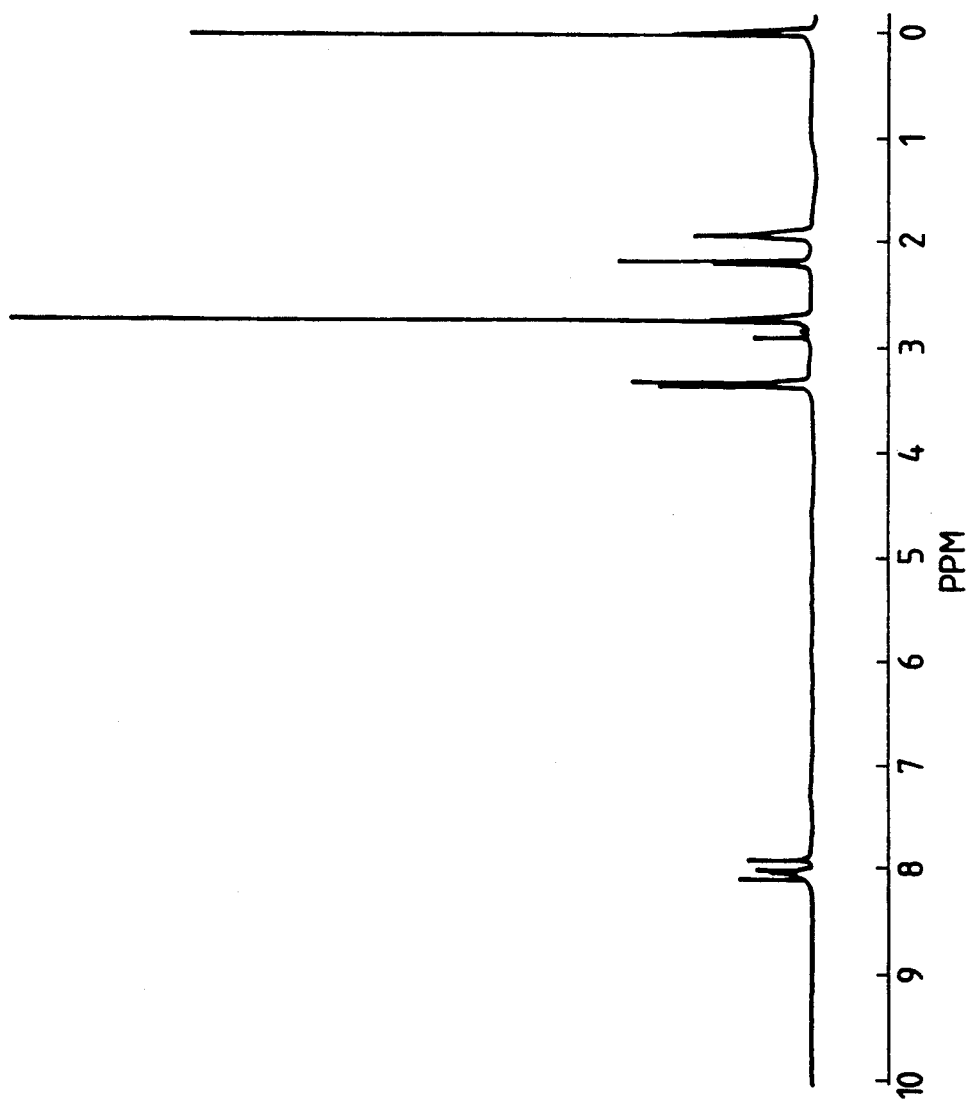
FIG. 3 is the proton NMR spectrum of s-BPDA/NMP complex.
Figure 4:
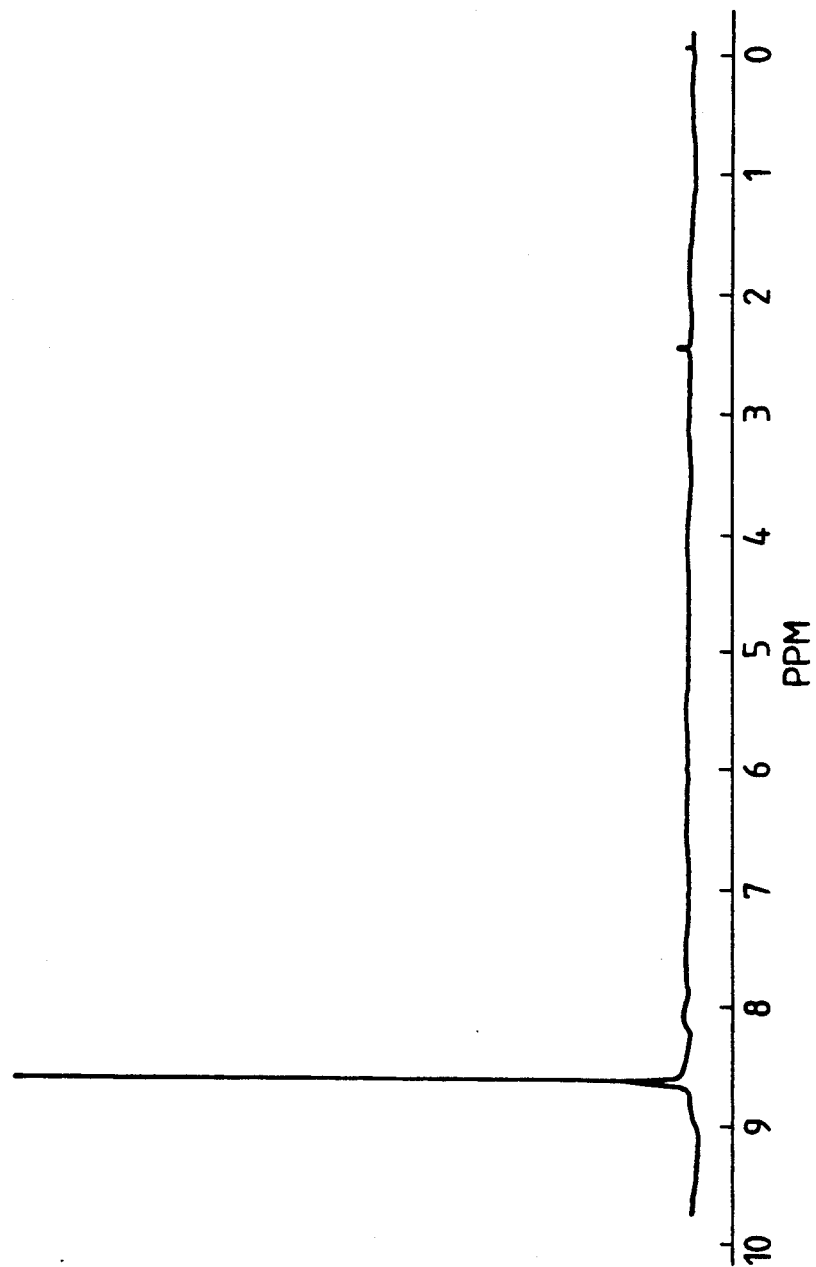
FIG. 4 is the proton NMR spectrum of PMDA.

An acid anhydride complex having an equivalent ratio 1:2 of s-BPDA:NMP was obtained nearly quantitatively by a reaction with s-BPDA and saturated NMP vapour in 40 hours at 200° C. The nuclear magnetic resonance spectrum of the obtained complex is shown in FIG. 3.

EXAMPLE 3

An acid anhydride complex having an equivalent ratio 1:2 of s-BPDA:TEA was obtained by a reaction with s-BPDA and saturated TEA vapour in 40 hours at 80° C.

EXAMPLE 4

An acid anhydride complex having an equivalent ratio 1:2 of PMDA: PY was obtained by a reaction with PMDA and saturated PY vapour in 40 hours at 100° C.

EXAMPLE 5

Figure 5:
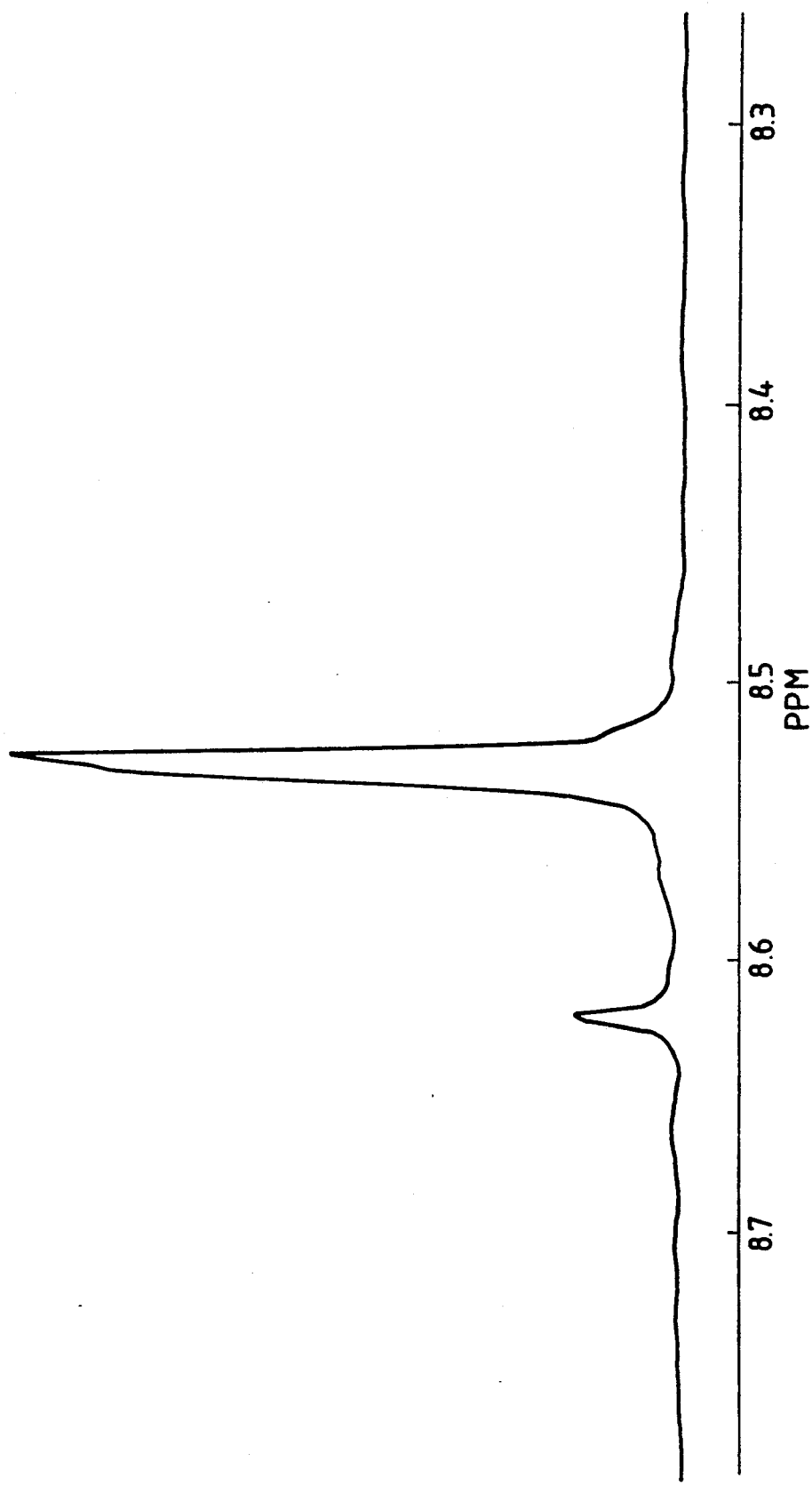
FIG. 5 is the proton NMR spectrum of PMDA/TEA complex.
Figure 6:
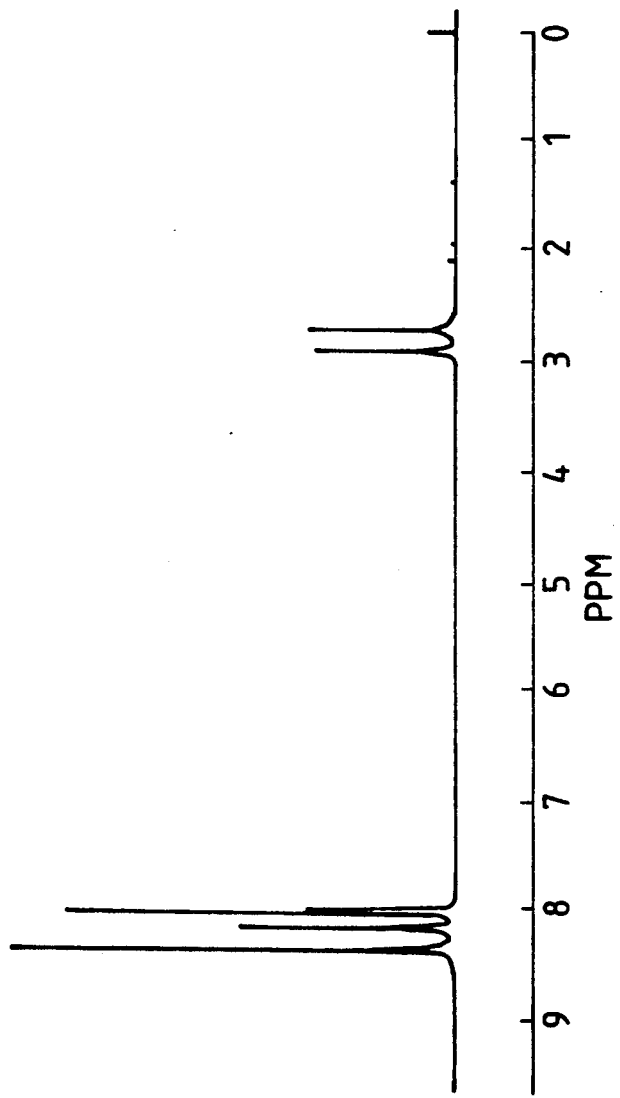
FIG. 6 is the proton NMR spectrum of 6FDA.

An acid anhydride complex having an equivalent ratio 1:2 of PMDA: TEA was obtained nearly quantitatively by a reaction with PMDA and saturated TEA vapour in 40 hours at 80° C. The nuclear magnetic resonance spectrum of the obtained PMDA complex is shown in FIG. 5.

EXAMPLE 6

An acid anhydride complex having an equivalent ratio 1:2 of PMDA: NMP was obtained nearly quantitatively by a reaction with PMDA and saturated NMP vapour in 40 hours at 200° C.

EXAMPLE 7

An acid anhydride complex having an equivalent ratio 1:2 of BTDA: PY was obtained nearly quantitatively by a reaction with BTDA and saturated PY vapour in 40 hours at 100° C. After heating the acid anhydride complex in DMSO 2 hours at 120° C., the yield of the acid anhydride complex was 75%.

EXAMPLE 8

Figure 7:
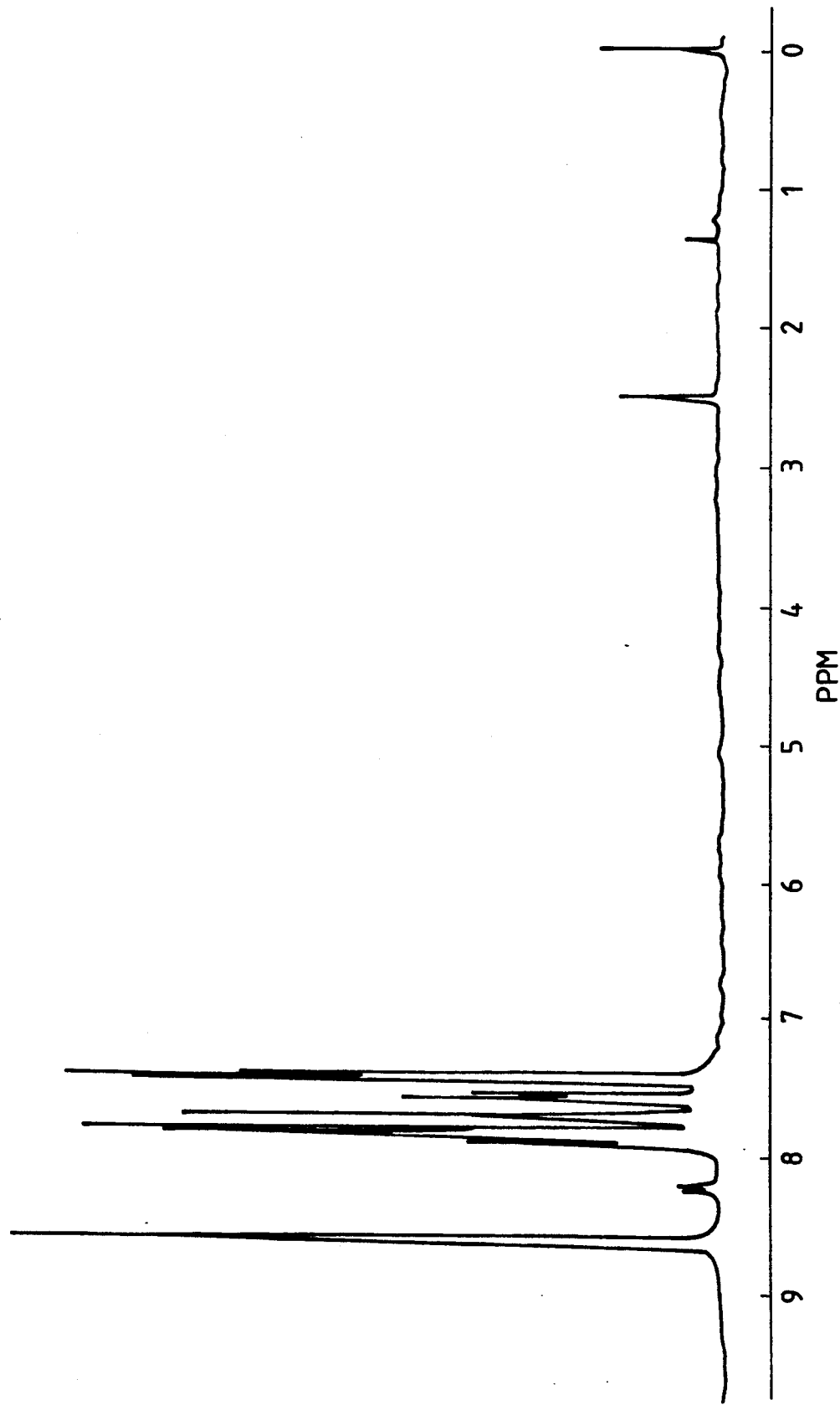
FIG. 7 is the proton NMR spectrum of 6FDA/PY complex.

An acid anhydride complex having a combination ratio 1:2 of 6FDA: PY was obtained nearly quantitatively by a reaction with 6FDA and saturated PY vapour in 40 hours at 100° C. The nuclear magnetic resonance spectrum of the obtained 6FDA complex is shown in FIG. 7.

EXAMPLE 9

An acid anhydride complex having an equivalent ratio 1:2 of 6FDA: TEA was obtained nearly quantitatively by a reaction with 6FDA and saturated TEA vapour in 40 hours at 80° C.

EXAMPLE 10

A reaction was occured by adding of NMP dropwise in 3 hours to 60 g. of s-BPDA powder with stirring under a condition heated at 80° C. -120° C. in inactive atmosphere, and a brown powder was obtained. The nuclear magnetic resonance spectrum of s-BPDA and the reaction product were measured. The formation of an acid anhydride complex was confirmed by observation of a peak shifting to lower magnetic field.

EXAMPLE 11

A reaction was occured by adding of DSMO dropwise in 3 hours to 60 g. of s-BPDA powder with stirring under a condition heated at 80° C. -120° C. in inactive atmosphere, and a brown powder was obtained. The nuclear magnetic resonance spectrum of the reaction product was measured. The formation of an acid anhydride complex was confirmed by observation of a peak shifting to lower magnetic field.

EXAMPLE 12

A reaction was occured by adding of THF and $\gamma$-propiolactam dropwise in 3 hours to 60 g. of s-BPDA powder with stirring under a condition heated at 80° C.-120° C. in inactive atmosphere, and a brown powder was obtained. The nuclear magnetic resonance spectrum of the reaction product was measured. The formation of an acid anhydride complex was confirmed by observation of a peak shifting to lower magnetic field. With other experiments which used lactams having different ring size from 5 to 10 under the same condition, the formation of acid anhydride complexes were confirmed by the observation of nuclear magnetic resonance spectrums. And in the case using N-methylacetamide, which is a same secondary amide as a lactam, the formation of a complex was also confirmed.

EXAMPLE 13

A mixture of 240 g. of THF and 6 g. of s-BPDA was heated 1-3 hours with PY in inactive atmosphere, and a yellow transparent solution was obtained. By adding the yellow solution to 20 times volume of n-hexane, a pale yellow substance was precipitated. The precipitate was separated from the liquid by filtration and was dried 12 hours at 60° C. in vacuum. A 7.2 g. of powder was obtained. The formation of a complex was confirmed by observation of a same peak shifting to lower magnetic field as shown in FIG. 2 in the nuclear magnetic resonance spectrum of the powder.

EXAMPLE 14

A mixture of 240 g. of caprolactam, 6 g. of s-BPDA, and $\gamma$-propiolactam was heated 1-3 hours in inactive atmosphere, and a yellow transparent solution of a complex was obtained. The formation of a complex was confirmed by observation of a same peak shifting to lower magnetic field as shown in FIG. 2 in the nuclear magnetic resonance spectrum of the solution.

EXAMPLE 15

The formation of a complex in the reaction product obtained by a same experiment as Example 10 except using BTDA instead of s-BPDA was confirmed by observation of a peak shifting to lower magnetic field in the nuclear magnetic resonance spectrum of the reaction product and BTDA.

EXAMPLE 16

The formation of a complex in the reaction product obtained by a same experiment as Example 10 except using PMDA instead of s-BPDA was confirmed by observation of a peak shifting to lower magnetic field in the nuclear magnetic resonance spectrum of the reaction product and PMDA.

Comparative Example 1

Figure 8:
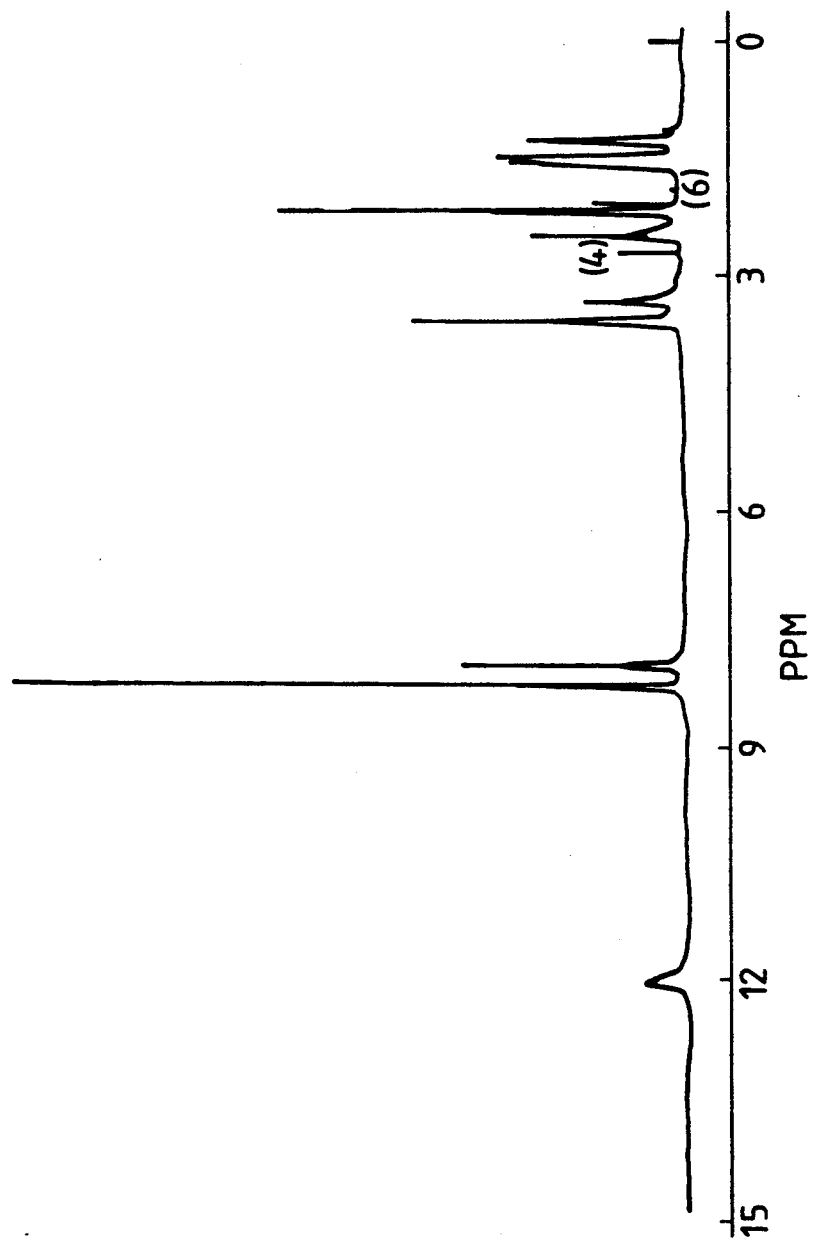
FIG. 8 is the proton NMR spectrum of bisimide compound.
Figure 9A:
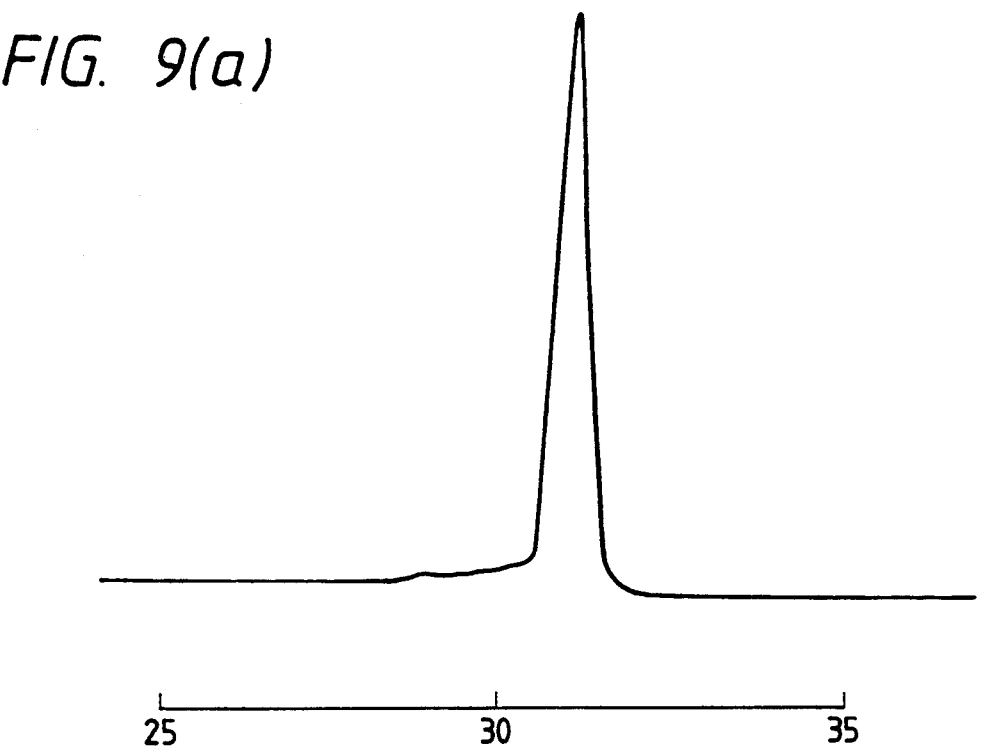
FIG. 9 (a) is the liquid chromatogram of s-BPDA.
Figure 9B:
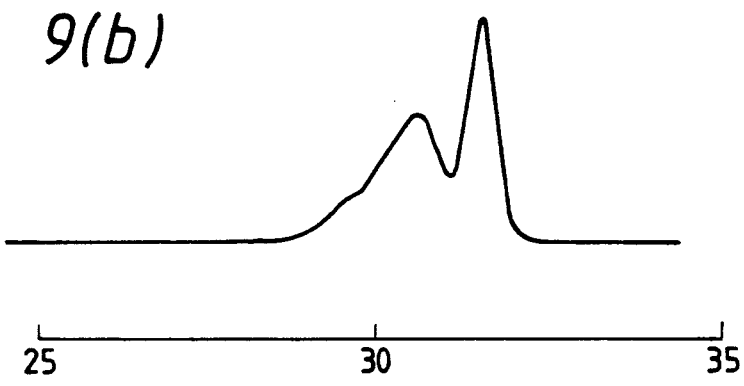
Figure 9C:
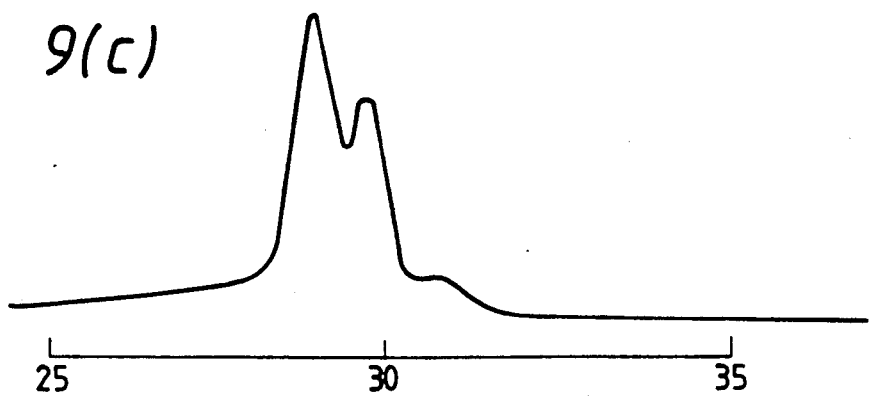

A mixture of 240 g. of NMP, 60 g. of s-BPDA, and $\epsilon$-caprolactam was heated 36 hours at 180° C.-200° C. in inactive atmosphere, and a brown solution was obtained. The nuclear magnetic resonance spectrum of the solution is shown in FIG. 8. The formation of any complex is not observed, but a quantitative formation of bisimide compound was confirmed. The time depending change of the yield of the product was measured by a chromatographic method, and the results are shown in FIG. 9(a) to FIG. 9(c). The reaction was very slow and the formation of bisimide carboxylic acid was scarsely observed in the reaction of 1-3 hours.

EXAMPLE 17

Figure 10:
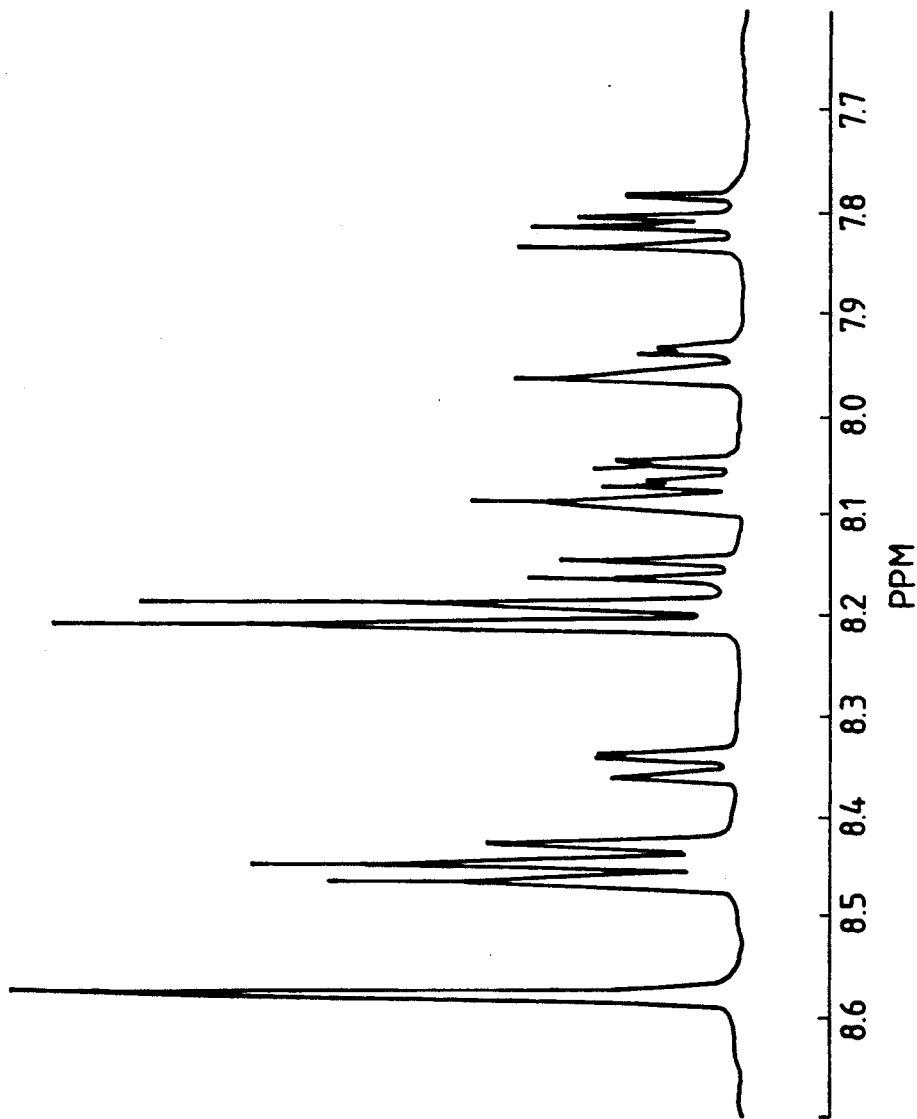
FIG. 10 is the proton NMR spectrum of s-BPDA/D-MSO complex at the moment after synthesizing.
Figure 11:
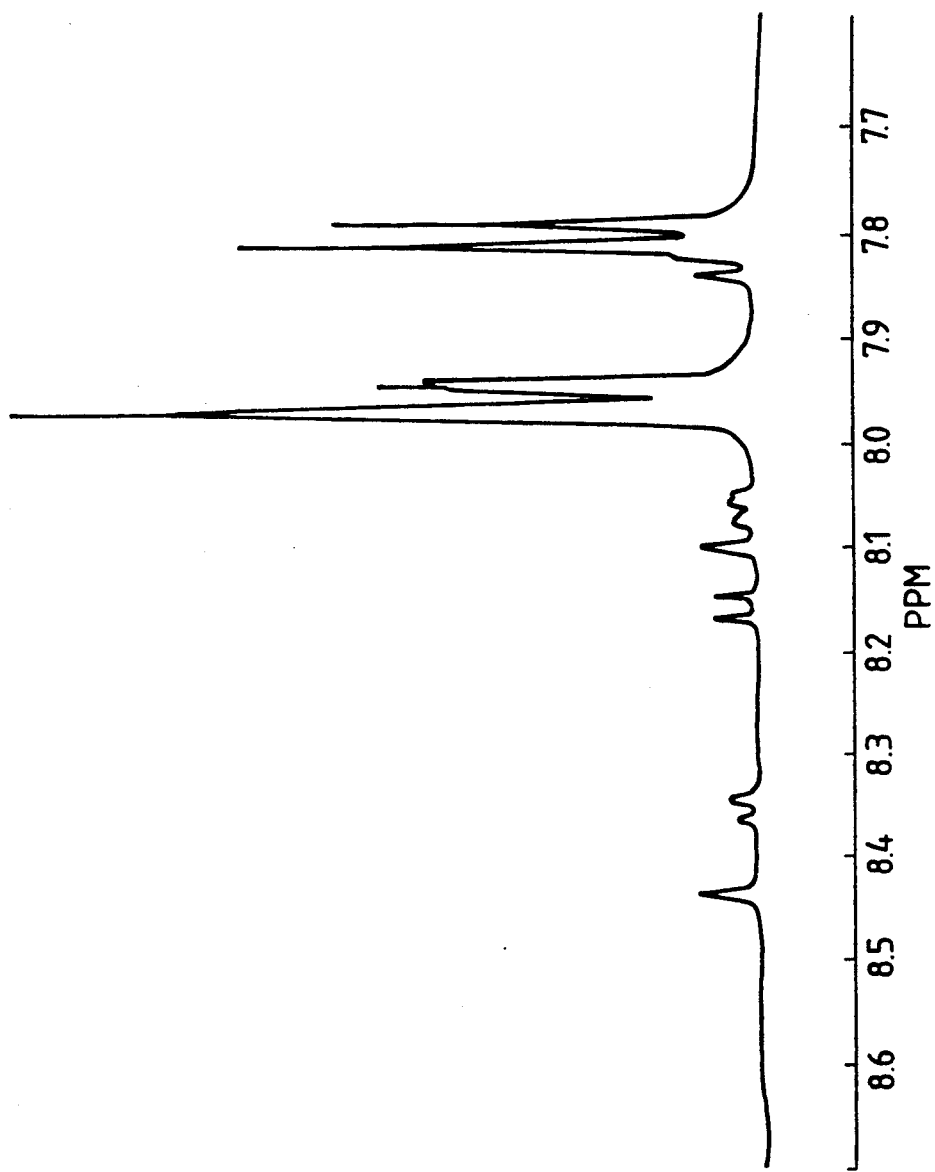
FIG. 11 is the proton NMR spectrum of s-BPDA/D-MSO complex after 18 hours from synthesis under moisture co-existent condition.

A mixture of s-BPDA and a complex comprising s-BPDA and DMSO was dissolved in DMSO contianing water. The changing of the composition was observed by measurement of nuclear magnetic resonance spectrum. The results are shown in FIG. 10 and FIG. 11. It was revealed that s-BPDA was hydrolized as the peaks of s-BPDA which were observed at the dissolution had been disappeared after 18 hours. On the other hand, the peaks of S-BPDA complex were observed even after 18 hours without any change. The result of the experiment mentioned above revealed that the formation of a complex achieved lowering of the hydrolizing property and significant stabilizing of s-BPDA.

EXAMPLE 18

A reaction was occured by adding slowly an equivalent p-PDA to a solution of s-BPDA complex which was obtained in Example 1 with stirring and ice-cooling. The viscosity of the varnish after the reaction of 3 hours with stirring was 8 poises at 30 wt. % of solid content.

EXAMPLE 19

A same experiment as Example 9 except using an equivalent DDE instead of p-PDA was held. The viscosity of the varnish obtained by the experiment was 15 poises at 30 wt. % of solid content.

EXAMPLE 20

A reaction was occured by adding slowly an equivalent p-PDA to a solution of a complex obtained in Example 4 in NMP with stirring. The viscosity of the varnish after the reaction of further 3 hours with stirring was 42 poises at 30 wt. % of solid content.

Comparative Example 2

A solution was prepared by dissolving 22 g. of p-PDA in 240 g. of NMP with stirring. A reaction was occured by adding an equivalent (60 g.) s-BPDA to the solution slowly with stirring by a stirrer connected to a motor and ice-cooling in inactive atmosphere. The viscosity of the reactant was increased as the addition of the solution was going on, and finally, at the time when total solution had added, it became impossible to stir the reactant because of increased viscosity.

Comparative Example 3

A same reaction as Comparative example 2 except using an equivalent (41 g.) of DDE instead of p-PDA was held. It became impossible to stir the reactant on the half way of the reaction.

EXAMPLE 21

A varnish which was obtained in Example 17 and applied on the surface of a glass substrate with an applicator was dried one hour at 100° C., and was hardened by heating up to 400° C. at the rate of 200° C./hour and kept 10 minutes at 400° C. A film obtained was cut out into a test piece of 5 mm × 50 mm, and its mechanical strength was measured. The break strength of the film was 36 kg./mm$^2$ and the break elongation was 25%. And the durable temperature defined as the temperature at which 3% loss in its weight occurs in 100 minutes was 520° C.

EXAMPLE 22

A varnish synthesized in Example 19 was hardened at 350° C. as the final hardening temperature and was measured the mechanical strength of the film. The break strength was 28 kg./mm$^2$ and the break elongation was 52%. The durable temperature defined same as Example 21 was 491° C.

EXAMPLE 23

A film was prepared from a varnish synthesized in Example 20 by the same process as Example 12 and was measured the mechanical strength. The break strength was 41 kg./mm$^2$ and break elongation was 22%. The durable temperature defined same as Example 20 was 517° C.

Comparative Example 4

A reaction was occurred by adding ⅔ of an equivalent (54.4 g.) s-BPDA slowly to a solution of 30 g. of p-PDA in 200 g. of NMP. The reaction was carried on further 5 hours after s-BPDA was added, and a dense green solution was obtained. By adding 27.2 g. of phthalic anhydride to the solution so as to make the ratio of amine and acid anhydride an equivalent and carrying on the reaction further 5 hours, a yellow transparent oligomer varnish having viscosity of 25 poises was obtained. The varnish was hardened by the same process as Example 20. In the hardening process, a large number of cracks were generated on the surface of the hardened body and any of film was not obtained. The measurement of mechanical strength was impossible.

Comparative Example 5

A reaction was occurred by adding ⅔ of an equivalent (31.3 g.) PMDA slowly to a solution of 50 g. of DDE in 200 g. of NMP. The reaction was carried on further 5 hours after PMDA was added, and a dense green solution was obtained. By adding 21.6 g. of phthalic anhydride to the solution so as to make the ratio of amine and acid anhydride an equivalent and carrying on the reaction further 5 hours, a yellow transparent oligomer varnish having viscosity of 19 poises was obtained. The varnish was hardened by the same process as Example 20. In the hardening process, a large number of cracks were generated on the surface of the hardened body same as comparative example 6 and any of film was not obtained. The measurement of mechanical strength was impossible.

Comparative Example 6

A half-esterified solution was synthesized by a reaction of 60 g. of s-BPDA and 2 times of an equivalent ethyl alcohol in 200 g. of NMP in 2 hours at 100° C. The solution was cooled down to room temperature and was added with an equivalent of p-PDA to s-BPDA. By dissolving the additives with stirring, a varnish having a half-ester as a functional group to cause polymerization in hardening process was obtained. The viscosity of the varnish was 1.8 poises. In the same hardening process as Comparative example 5, a large number of cracks were generated on the surface of the hardened body and any of film was not obtained. The measurement of mechanical strength was impossible.

Comparative Example 7

A varnish solution having a concentration of 40 wt. % and viscosity of 42 poises was obtained by dissolving a resin having ethynyl groups at the terminal of the molecular chain in NMP. The varnish was hardened by the same process as Example 21. An obtained film was too fragile to be measured the mechanical strength.

EXAMPLE 24

Figure 12:
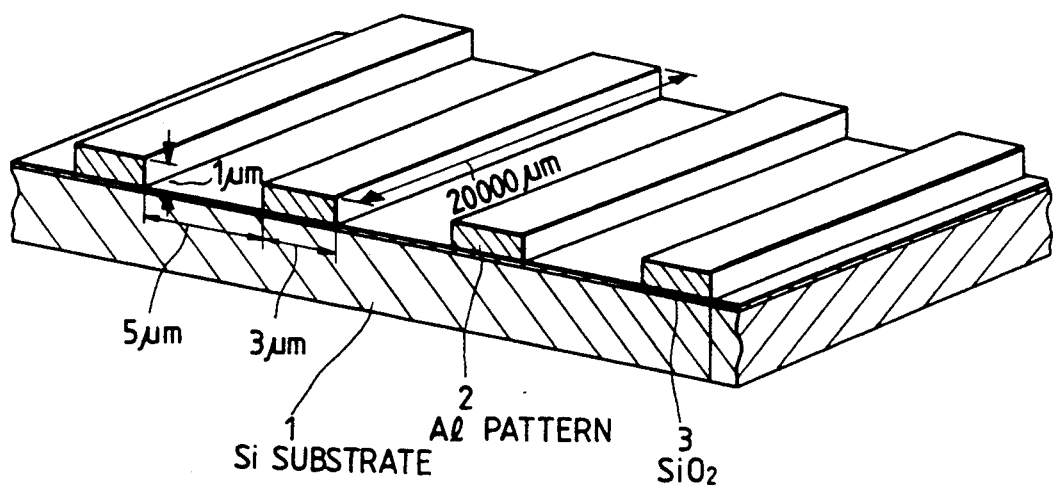
FIG. 12 is a perspective illustration showing the structure of the evaluation pattern to be used for the measurement of flatness of a polyimide film produced from acid dianhydride by a process of the present invention.

The result of the measurement of flatness of a film produced from the varnish synthesized in Example 17 by applying it on the surface of an aluminum pattern of which structure is shown in FIG. 12 and hardened there was 0.80. The flatness is defined by the following equation and the value is more preferable as it close to 1.

$$P = 1 - \frac{\Delta H}{H} \quad (3)$$

Figure 13:
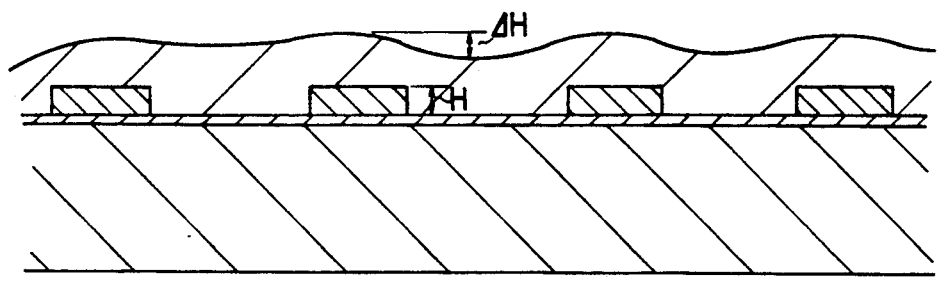
FIG. 13 is a cross sectional view showing the definition of the flatness of a polyimide film.

The symbols in the equation (3) are defined in FIG. 13. The evaluation pattern to be used for the measurement of the flatness of a polyimide film is shown in FIG. 12. Using the pattern, the flatness of a film produced on the surface of the pattern was measured according to the definition shown in FIG. 13.

EXAMPLE 25

The result of the measurement of flatness of a film produced from the varnish synthesized in Example 18 by applying it on the surface of an aluminum pattern of which structure is shown in FIG. 12 and hardened there was 0.83.

Comparative Example 8

A polyamic acid varnish having a concentration of 15 wt. % which was synthesized from p-PDA and s-BPDA by a conventional process was applied and hardened by the same process as Example 25, and the flatness of the film was measured. The result was 0.44.

EXAMPLE 26

A transparent brown solution of a complex was obtained by adding 6 g. of BTDA to 240 g. of THF and heating 1-3 hours with DMSO in inactive atmosphere. The formation of a complex was confirmed by observation of the nuclear magnetic resonance spectrum of the solution which was measured after the same treatment as Example 13.

EXAMPLE 27

A transparent brown solution of a complex was obtained by adding 6 g. of BTDA and γ-propiolactam to 240 g. of THF and heating 1-3 hours in inactive atmosphere. In the nuclear magnetic resonance spectrum measured after the same treatment as Example 13, a peak shifting to lower magnetic field was observed and the formation of a complex was confirmed. And in the same experiment except using different ring size of lactam from 5 to 10, the formation of a complex was confirmed by the nuclear magnetic resonance spectrum. And in the case of using N-methylacetamide, the formation of a complex was also confirmed.

EXAMPLE 28

A transparent yellow solution was obtained by adding 6 g. of BTDA to 240 g. of THF and heating 1-3 hours with PY in inactive atmosphere. A yellow precipitate was obtained by adding the solution to 20 times volume of n-hexane. After the same treatment as Example 13, the nuclear magnetic resonance spectrum was measured. In the spectrum, a peak shifting to lower magnetic field was observed and the formation of a complex was confirmed.

EXAMPLE 29

A transparent yellow solution of a complex was obtained by adding of 6 g. of BTDA and γ-propiolactam to 240 g. of caprolactone and heating 1-3 hours in inactive atmosphere. After the same treatment as Example 13, the nuclear magnetic resonance spectrum was measured. A peak shifting to lower magnetic field was observed and the formation of a complex was confirmed.

Comparative Example 9

A brown solution was obtained by adding 6 g. of BTDA and ε-caprolactam to 240 g. of NMP and heating 36 hours at 180° C.-200° C. in inactive atmosphere. According to the nuclear magnetic resonance spectrum of the solution, the formation of a complex was not observed, but quantitative yield of bisimide compound was confirmed. By measuring the time depending change of the yield of the product by a liquid chromatographic method, it was revealed that the reaction went on very slowly and the formation of bisimide carboxylic acid was scarcely observed in the reaction of 1-3 hours.

EXAMPLE 30

A mixture of BTDA and a complex comprising BTDA and DMSO was dissolved into DMSO containing water, and the change of the solution was measured with a nuclear magnetic resonance spectrum. The result revealed that the peaks of BTDA which was observed at the moment of dissolving disappeared after 18 hours and hydrolysis of BTDA had occurred. On the other hand, the peaks of the complex including BTDA was observed even after 18 hours without any change, and it was confirmed that the formation of a complex achieved lowering of hydrolyzing property and significant stabilizing of BTDA.

EXAMPLE 31

A transparent brown solution of a complex was obtained by adding 60 g. of DSDA to 240 g. of THF and heating 3 hours with NMP in inactive atmosphere. According to the nuclear magnetic resonance spectrum which was measured after the solution was treated by the same process as Example 13, a peak shifting to lower magnetic field was observed and the formation of a complex was confirmed.

EXAMPLE 32

A transparent brown solution of a complex was obtained by adding 6 g. of DSDA to 240 g. of THF and heating 3 hours with DMSO in inactive atmosphere. According to the nuclear magnetic resonance spectrum which was measured after the solution was treated by the same process as Example 13, a peak shifting to lower magnetic field was observed and the formation of a complex was confirmed.

EXAMPLE 33

After adding 60 g. of DSDA and γ-propiolactam to 240 g. of THF, the solution was heated 3 hours in inactive atmosphere. After the solution was treated by the same process as Example 13, a nuclear magnetic resonance spectrum was measured. A peak shifting to lower magnetic field was observed in the spectrum and the formation of a complex was confirmed. And in the same experiment except changing the ring size of lactams to 5-10, the formation of a complex was confirmed with the nuclear magnetic resonance spectrum. And in the case of using N-methylacetamide which is a same secondary amine as lactam, the formation of a complex was also confirmed.

EXAMPLE 34

A transparent yellow solution was obtained by adding 6 g. of DSDA to 240 g. of THF and heating 3 hours with PY in inactive atmosphere. A pale yellow precipitate was obtained by adding the solution into 20 times of volume of n-hexane. After the precipitate was treated with the same process as Example 4, a nuclear magnetic resonance spectrum was measured. A peak shifting to lower magnetic field was observed and the formation of a complex was confirmed.

EXAMPLE 35

A transparent yellow solution was obtained by adding 60 g. of DSDA and γ-propiolactam to 240 g. of caprolactone and heating 3 hours with γ-propiolactam in inactive atmosphere. After the precipitate was treated with the same process as Example 4, the nuclear magnetic resonance spectrum was measured. A peak shifting to lower magnetic field was observed and the formation of a complex was confirmed.

Comparative Example 10

A brown solution was obtained by adding 60 g. of DSDA and ε-caprolactam to 240 g. of NMP and heating 36 hours at 180° C.-200° C. in inactive atmosphere. According to the nuclear magnetic resonance spectrum of the solution, the formation of a complex was not observed, but the quantitative formation of bisimide carboxylic acid was confirmed. The reaction went on slowly and the formation of bisimide carboxylic acid was scarcely observed in the reaction of 1-3 hours.

EXAMPLE 36

A mixture of DSDA and a complex of DSDA was dissolved into DMSO containing water and change of the solution was measured with the nuclear magnetic resonance spectrum. The peak of DSDA which was observed at the moment of dissolution disappeared after 18 hours and hydrolysis of DSDA was confirmed. On the other hand, the peak of a complex of DSDA was observed even after 18 hours without any change. The result revealed that the formation of a complex achieved lowering of hydrolyzing property and significant stabilizing of DSDA.

EXAMPLE 37

A transparent brown solution of a complex was obtained by adding 60 g. of 6FDA to 240 g. of NMP and heating 3 hours at 80° C.-120° C. in inactive atmosphere. In the nuclear magnetic resonance spectrum of 6FDA and of the solution, a peak shifting to lower magnetic field was observed and the formation of a complex was confirmed.

EXAMPLE 38

A transparent brown solution of a complex was obtained by adding 6 g. of 6FDA to 240 g. of THF and heating 3 hours with DMSO in inactive atmosphere. After the solution was treated by the same process as Example 4, the nuclear magnetic resonance spectrum was measured. A peak shifting to lower magnetic field was observed and the formation of a complex was confirmed.

EXAMPLE 39

A transparent brown solution of a complex was obtained by adding 60 g. of 6FDA and γ-propiolactam to 240 g. of THF and heating 3 hours in inactive atmosphere. And after the solution was treated with the same process as Example 4, the nuclear magnetic resonance spectrum was measured. The formation of a complex was confirmed by the observation of a peak shifting to lower magnetic field in the spectrum. And, in the same experiment except changing the ring size of lactam to 5-10, the formation of a complex was confirmed with the nuclear magnetic resonance spectrum. And also, in an experiment using N-methylacetamide which is same secondary amide as lactam, the formation of a complex was confirmed.

EXAMPLE 40

A transparent yellow solution was obtained by adding 6 g. of 6FDA to 240 g. of THF and heating 3 hours in inactive atmosphere. According to the nuclear magnetic resonance spectrum measured after the solution was treated by the same process as Example 4, a peak shifting to lower magnetic field was observed and the formation of a complex was confirmed.

EXAMPLE 41

A transparent yellow solution of a complex was obtained by adding 60 g. of 6FDA and γ-propiolactam to 240 g. of caprolactone and heating 3 hours in inactive atmosphere. According to the nuclear magnetic resonance spectrum measured after the solution was treated by the same process as Example 4, the same peak shifting to lower magnetic field as seen in FIG. 2 and 3 was observed and the formation of a complex was confirmed.

Comparative Example 11

A brown solution was obtained by adding 60 g. of 6FDA and ε-caprolactam to 240 g. of NMP and heating 36 hours at 180° C.-200° C. in inactive atmosphere. According to the nuclear magnetic resonance spectrum of the solution, the formation of any complex was not observed. But, the quantitative formation of bisimide compound was confirmed. The time depending change of the yield of the product was measured with a liquid chromatographic method, and it was revealed that the reaction went on very slowly and the formation of bisimide carboxylic acid was scarcely observed in reaction of 1-3 hours.

EXAMPLE 42

A mixture of 6FDA and a complex comprising 6FDA and DMSO was dissolved into DMSO containing water and a change of the solution was measured with a nuclear magnetic resonance spectrum. The peaks of 6FDA, which was observed at the time of the dissolution, was disappeared after 18 hours and hydrolysis of 6FDA was confirmed. On the other hand, the peak of the complex was observed without any change. With this observation, it was confirmed that the formation of a complex achieved lowering of hydrolizing property and significant stabilizing of 6FDA.

What is claimed is:

1. A complex consisting essentially of an aromatic acid dianhydride and an organic base substance coordinated with the dianhydride, said base substance having a donor number of at least 20 and being free from an active hydrogen atom therein, wherein the complex has an endothermic peak of 102° to 257° C.

2. The complex as claimed in claim 1, wherein said base substance has the donor number of at least 25.

3. A complex according to claim 1, wherein said complex is represented by the following general formula:

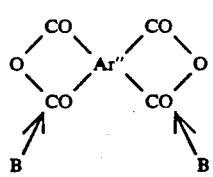

wherein Ar" is a residual group of a carboxylic dianhydride and B is the organic base substance coordinated with the dianhydride.

4. A complex according to claim 1, wherein said complex is represented by the general formula:

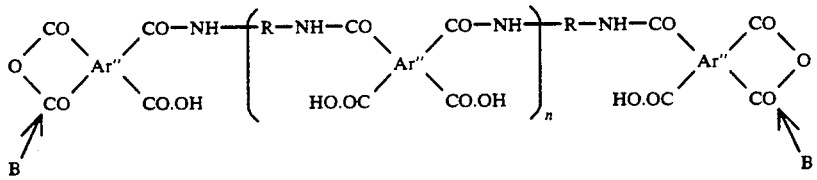

wherein Ar'' is a residual group of a carboxylic dianhydride, R is an organic residue group of an amine and n is 0 or an integer of at most 20 and B is the organic base substance coordinated with the dianhydride.

5. A process for preparing a composition comprising a complex consisting essentially of an aromatic acid dianhydride and an organic base substance coordinated with the dianhydride, which comprises contacting an aromatic acid dianhydride with a base substance having a donor number of at least 20 and being free from an active hydrogen atom therein, at an elevated temperature for a time sufficient to form the complex, wherein the complex has an endothermic peak of 102° to 257° C.

6. A process according to claim 5, which comprises contacting a carboxylic dianhydride Ar with a base substance B having a donor of at least 20 and being free from an active hydrogen atom in the molecule in such a manner that the dianhydride Ar and the compound B are broader to contact in the gaseous state, thereby forming a complex represented by the general formula:

Ar.aB (wherein $2 \geq a > 1$)

said complex having a coordinate bond between the carbon atom and the carbonyl group of the carboxylic dianhydride and said base substance B.

7. The process according to claim 5, wherein said carboxylic dianhydride is contacted with said base substance in the vapor phase.

* * * * *